United States Patent
Kinoshita et al.

(10) Patent No.: US 7,167,803 B2
(45) Date of Patent: Jan. 23, 2007

(54) VESSEL INSPECTION METHOD AND VESSEL INSPECTION DEVICE

(75) Inventors: Shigehiro Kinoshita, Tokyo (JP); Toshiro Ishida, Tokyo (JP); Yuzo Otsuka, Tokyo (JP); Toshio Moriya, Tokyo (JP)

(73) Assignee: Tetra Labal Holdings & Finance S.A., Pully (CH)

( * ) Notice: Subject to any disclaimer, the term of this patent is extended or adjusted under 35 U.S.C. 154(b) by 0 days.

(21) Appl. No.: 10/532,115

(22) PCT Filed: Oct. 16, 2003

(86) PCT No.: PCT/JP03/13230

§ 371 (c)(1),
(2), (4) Date: Oct. 17, 2005

(87) PCT Pub. No.: WO2004/038393

PCT Pub. Date: May 6, 2004

(65) Prior Publication Data

US 2006/0109013 A1    May 25, 2006

(30) Foreign Application Priority Data

Oct. 22, 2002    (JP) .............................. 2002-306841

(51) Int. Cl.
*G01R 22/08* (2006.01)
(52) U.S. Cl. ....................................................... 702/35
(58) Field of Classification Search .................. 702/35; 73/592; 324/456; 356/237; 607/175; 600/176
See application file for complete search history.

(56) References Cited

U.S. PATENT DOCUMENTS 4,256,028 A * 3/1981 Amberg ...................... 493/287

FOREIGN PATENT DOCUMENTS

| JP | 59-154641 | 10/1984 |
|---|---|---|
| JP | 7-146251 | 6/1995 |
| JP | 8-301241 | 11/1996 |
| JP | 9-207921 | 8/1997 |
| JP | 2002-189021 | 7/2002 |

\* cited by examiner

*Primary Examiner*—John Barlow
*Assistant Examiner*—Tung S. Lau
(74) *Attorney, Agent, or Firm*—Buchanan Ingersoll & Rooney PC (57) ABSTRACT

The object of the invention is to provide a container inspection method and a container inspection device which is not container quality inspection by individual and operator's empirical approach, not influenced by operator's skillfulness, can eliminate human error such as missing when recording and error in writing, not based on operator's subjective judgment, whose result is objective, and easily and statistically stores objective data. The container inspection method and container inspection device comprises an inspection for a container formed of a web-like packaging laminated material, which includes peeling flaps from the container wall by a pre-processing unit, cutting the container wall to prepare a sampled body by a sampled body preparing unit, inspecting seal quality by a seal quality unit, inspecting seal zone by an image processing unit, and inspecting damage on the seal zone by a seal damage inspection unit.

4 Claims, 7 Drawing Sheets

VESSEL INSPECTION METHOD AND VESSEL INSPECTION DEVICE

TECHNICAL FIELD

This invention relates to a container inspection method and a container inspection device for inspecting quality of paper-made container and the like filled with liquid food such as juice and milk.

TECHNICAL BACKGROUND

In some packaging and filling systems of paper-made containers filled with liquid food such as juice and milk, final shapes of the containers are obtained by forming web-like packaging laminated materials having predetermined folding lines in tubular shape, lapping both ends of the packaging material and forming overlap, longitudinally sealing in the longitudinal direction of the tube by the overlap, filling food into the tubular packaging material, pressing the tubular packaging material in the predetermined intervals to seal the material by transversal seal in transversal direction, cutting at the center of the transversal seal zone to obtain a pillow-like preliminary forming, and sealing flaps containing the transversal seal zone formed by folding along the folding lines to side wall of the container and bottom face of the container.

Figure 1:
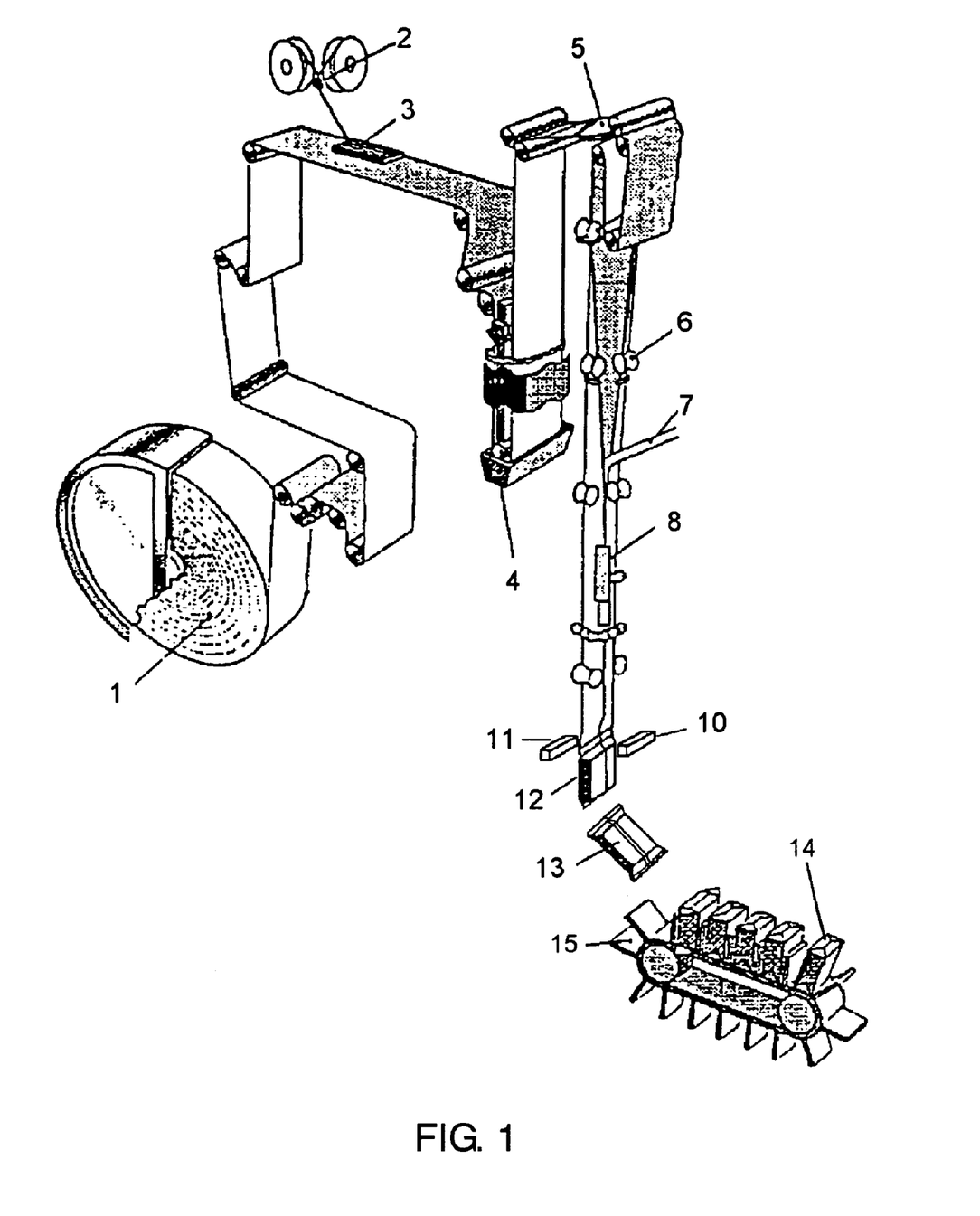
FIG. 1 is an overview of a packaging filling machine for paper packaging container.

FIG. 1 shows an outline of one example of a filling packaging machine for the paper-made container. The filling machine shown in this example winds out a packaging material web 1 having thermoplastic material layer on the inner and outer layers, wound in roll shape, transfers it in the filling machine by rollers, bonds a trip tape 2 to one end of the packaging material web by a strip tape applicator 3, passes the packaging material web in a sterilizing bath 4 and sterilizes, removes the sterilizing agent by an air knife 5, forms the tubular packaging material by a forming roller 6, forms an overlap by lapping both ends of the packaging material, longitudinally seals the overlap in the tube longitudinal direction by a longitudinal seal element 8 to form a longitudinal seal zone, fills liquid food into the tube from a filling pipe 7, sandwiching this tube by a sealing jaw 10 and an oppositely arranged jaw 11 while sending this tube downward by a length equivalent to one packaging container, forms two transversal seal zones by transversally sealing in the crossing direction, at the same time continuously forms pillow-like preliminary forming 12, cuts middle of the seal zone of the connected pillow-like preliminary forming by knife or the like to separate to individual pillow-like preliminary forming 13, bends flaps on the upper and lower of the separated pillow-like preliminary forming at a final folder 15 to form a finally shaped packaging filling container 14.

Figure 2:
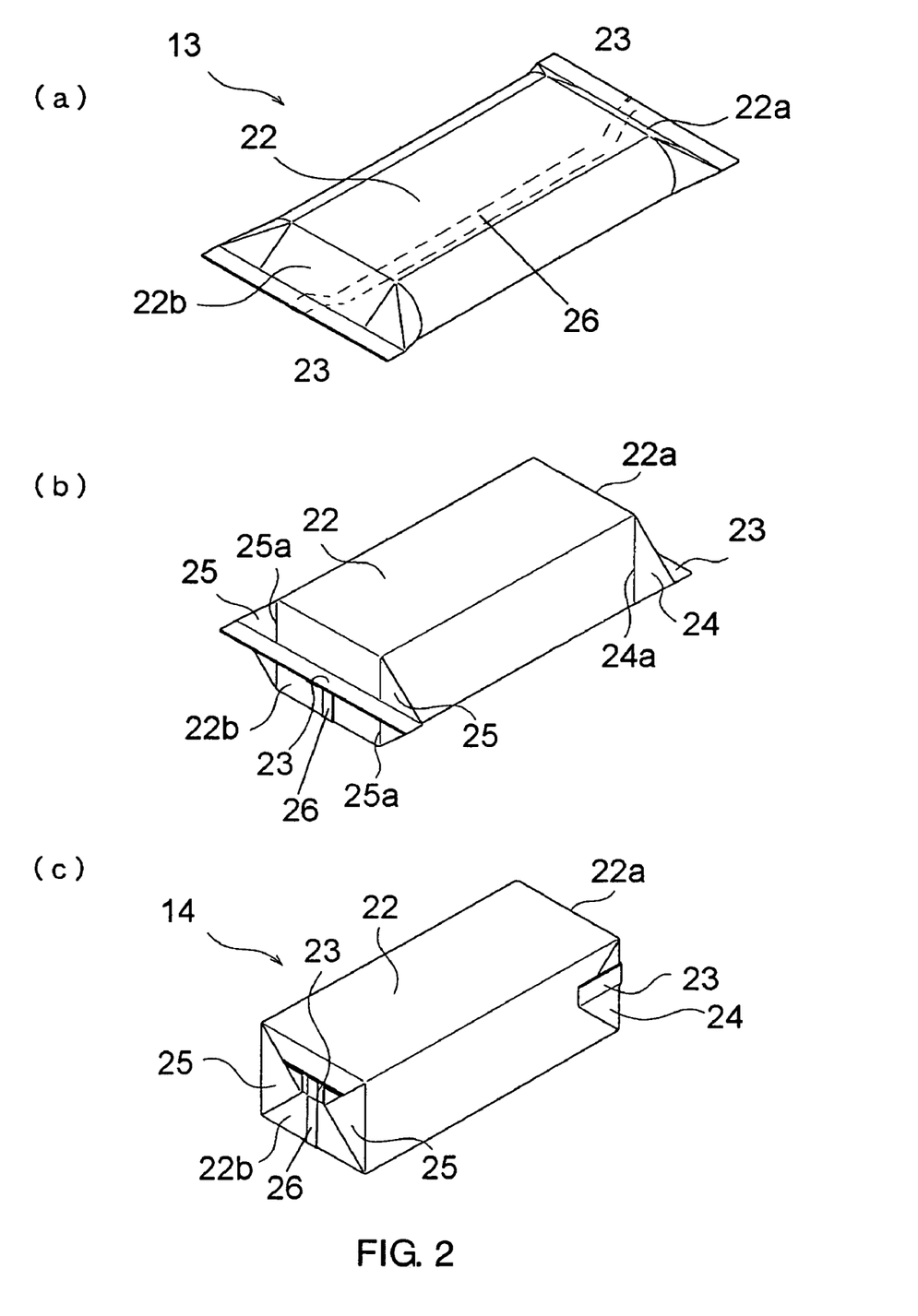
FIG. 2 is an overview explaining an aspect to form a finally shaped paper packaging container from a preliminary forming.
Figure 3:
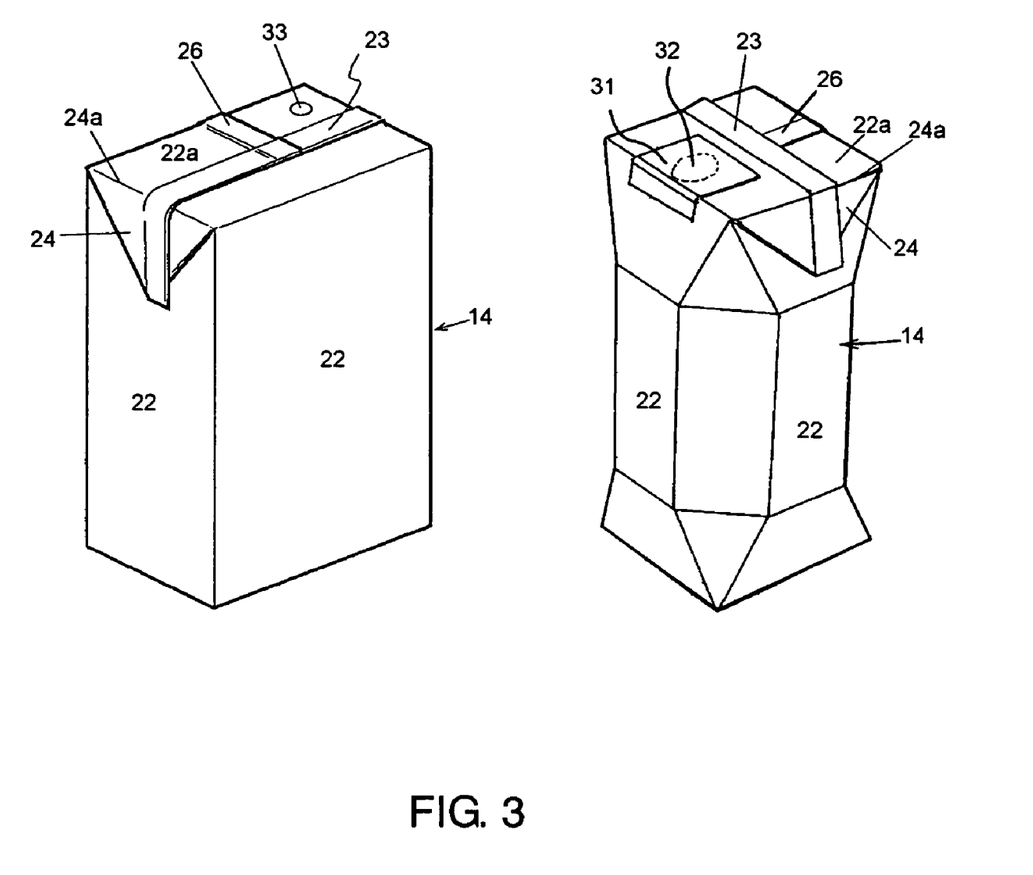
FIG. 3 is an overview of an example of a paper packaging container.

FIG. 2 shows an aspect in which the pillow-like preliminary forming 13 is folded at the final folder 15. The pillow-like preliminary forming 13 is sealed by two transversal (transversal line) seal zone 23 and longitudinal seal zone 26. The pillow-like preliminary forming 13 has side walls 22, 22zone 22a defined by the folding lines (refer to FIG. 2(a)). As shown in FIG. 2(b), the main body of the pillow-like preliminary forming is formed in rectangular solid along the folding lines. On the edge, the transversal seal zone 23 and flaps 24, 25 are formed to be upright from the container wall. The transversal seal zone 23 is upright from the bottom face 22zone the top face 22a. The flaps 24 and 25 integrally communicate with the container wall through ridge sides 25a and 24a. Next, as shown in FIG. 2(c), after the transversal seal zone 23 is folded, the flaps are rotated around the ridge side as a center, a container top side flap 24 is folded into the side wall 22, and the container bottom side flap 25 is folded into the bottom face 22b. FIG. 3 shows perspective views of outline of a rectangular solid liquid food filling paper-made container (FIG. 3(a)) according to the folded aspect shown in FIG. 2, and a liquid food filling paper-made container (FIG. 3(b)) whose main body center is octangular column according to a similar aspect. The containers 14 have a folded transversal seal zone 23, container walls 22 and 22a and a longitudinal seal zone 26 running to the bottom face from the top wall 22a through the container wall on the back, and is provided with the flap 24 folded through the ridge side 24a. Each container has a straw penetrating sealing hole 33, a faucet 32 and a sealing pull-tab 31.

Sufficient sealing must be carried out at said seal zone so as to prevent the liquid food contained in the container from leaking and being exposed to external air. However, if the temperature and pressure on the transversal seal are improper, the melted thermoplastic material on the packaging laminated material may protrude into the container into which the content is filled. The melting substance directly contacts the contained liquid foods, and becomes brittle by sharply cooling, and the laminated material may be broken from the protruded location. For sealing, it is necessary to obtain a transversal seal whose melted substance does not protrude into the container. In addition, for forming, stress may be concentrated on the formed portion or folded portion, thereby causing damages such as pinhole and crack. And further, damage of sealing defect may be caused. Then, liquid food containers commercialized by the filling packaging machine are regularly and individually sampled by the operator of the machine for inspection, and the sampled container, whose flap is peeled, is deformed to pillow-like shape from rectangular solid shape, and then inspected for seal strength, presence or absence of pinhole, and further overlap width of the longitudinal seal depending on empirical procedure of the operator.

DISCLOSURE OF THE INVENTION

The above individual and operator's empirical procedure is an inspection combining manually peeling inspection, pinhole inspection by ink dying and continuity test and the like, further visual inspection by operator. However, the quality inspection greatly depends on empirical factor, which largely loads on operator, and likely causing human errors such as missing when recording and error in writing. Because inspection by empirical procedure is based on the operator's subjective judgment, the results vary with individual person and it is difficult to statistically store the objective data. This invention is intended to provide a container inspection method and a container inspection device which is not a container quality inspection method by individual and operator's empirical procedure, not influenced by operator's skillfulness, and can eliminate human error such as missing when recording and error in writing, is not based on operator's subjective judgment, and whose results are objective, further which easily and statistically stores objective data.

A container inspection method and container inspection device according to this invention is an inspection for a finally shaped and sealed container obtained by forming a web-like packaging laminated material having predetermined folding lines in tube shape, lapping both ends of the packaging material to form an overlap, longitudinally sealing the packaging material in the longitudinal direction to form an longitudinal seal zone on the overlap, filling food into the tube-shaped packaging material, pressing the packaging material at every predetermined interval in the crossing direction to seal the material by the transversal seal to form a transversal seal zone, cutting at the middle of the transversal seal zone to obtain a pillow-like preliminary forming, and sealing flaps formed by folding along the folding lines to the container side wall and/or a container bottom face, comprising:

rotating the flaps sealed to the container wall around a ridge side where the flaps integrally communicate with the container wall to peel the flaps from the container wall;

returning to a shape of the pillow-like preliminary forming by a pre-processing unit;

cutting the container wall, squeezing out the filled food to prepare the sampled body by a sampled body preparing unit;

measuring electrostatic capacity and loss factor on said seal zone of the sampled body to inspect seal quality by a seal quality unit;

measuring an overlap width on the seal inspected sampled body and unevenness on the external surface of the transversal seal zone edge on the inside of the container by an image processing unit to inspect the overlap width and the unevenness by image processing;

arranging a first electrode at a distance from said seal zone of the sampled body;

arranging a second electrode so as to contact said sampled body; and inspecting damage on the seal zone by a seal damage inspection unit based on feedback current flowing on the second electrode.

This allows for a container inspection method and container inspection device which is not a container quality inspection method by individual and operator's empirical procedure, not influenced by operator's skillfulness, and can eliminate human error such as missing when recording and error in writing, is not based on operator's subjective judgment, and whose results are objective, further which easily and statistically stores objective data.

A container inspection method according to this invention is a method for inspecting a finally shaped and sealed container obtained by forming a web-like packaging laminated material having predetermined folding lines in tube shape, lapping both ends of the packaging material to form an overlap, longitudinally sealing the packaging material in the longitudinal direction to form an longitudinal seal zone on the overlap, filling food into the tube-shaped packaging material, pressing the packaging material at every predetermined interval in the crossing direction to seal the packaging material by the transversal seal to form a transversal seal zone, cutting at the middle of the transversal seal zone to obtain a pillow-like preliminary forming, and sealing flaps formed by folding along the folding lines to the container side wall and/or a container bottom face, comprising:

rotating the flaps sealed to the container wall around a ridge side where the flaps integrally communicate with the container wall to peel the flaps from the container wall;

returning to a shape of the pillow-like preliminary forming;

cutting the container wall, squeezing out the filled food to prepare the sampled body;

measuring electrostatic capacity and loss factor on said seal zone of the sampled body to inspect seal quality;

measuring an overlap width on the seal inspected sampled body and unevenness on the external surface of the transversal seal zone edge on the inside of the container by an image processing unit to inspect the overlap width and the unevenness by image processing;

arranging a first electrode at a distance from said seal zone of the sampled body;

arranging a second electrode so as to contact said sampled body; and inspecting damage on the seal zone based on feedback current flowing on the second electrode.

A preferred embodiment of the container inspection method according to this invention processes the inspection results of said seal quality inspection, inspection by image processing and inspection for damage on the seal zone, stores and further outputs.

A container inspection device according to this invention is a device for inspecting a finally shaped and sealed container obtained by forming a web-like packaging laminated material having predetermined folding lines in tube shape, lapping both ends of the packaging material to form an overlap, longitudinally sealing the packaging material in the longitudinal direction to form a longitudinal seal zone on the overlap, filling food into the tube-shaped packaging material, pressing the packaging material at every predetermined interval in the crossing direction to seal the material by the transversal seal to form a transversal seal zone, cutting at the middle of the transversal seal zone to obtain a pillow-like preliminary forming, and sealing flaps formed by folding along the folding lines to the container side wall and/or a container bottom face, comprising:

a pre-processing unit for rotating the flaps sealed to the container wall around a ridge side where the flaps integrally communicate with the container wall to peel the flaps from the container wall, and for returning to a shape of the pillow-like preliminary forming;

a sampled body preparing unit for cutting the container wall and squeezing out the filled food to prepare the sampled body;

a seal quality unit for measuring electrostatic capacity and loss factor on said seal zone of the sampled body to inspect seal quality;

an image processing unit for measuring an overlap width on the seal inspected sampled body and unevenness on the external surface of the transversal seal zone edge on the inside of the container to inspect the overlap width and the unevenness by image processing; and, a seal damage inspection unit for arranging a first electrode at a distance from said seal zone of the sampled body, arranging a second electrode so as to contact said sampled body, and inspecting damage on the seal zone based on feedback current flowing on the second electrode.

A preferred embodiment of the container inspection device according to this invention comprises a control sorting unit for controlling said seal quality unit, image processing unit and seal damage inspection unit, receiving the judging result according to the command signal and sorting said sampled body according to acceptability of the judging result.

BEST MODE FOR CARRYING OUT THE INVENTION

An embodiment of this invention will be described below with reference to the drawings.

A packaging filling device used in this embodiment is a packaging filling device as shown in FIG. 1. This embodiment winds out a packaging material web 1 having predetermined folding lines, wound in roll shape, forms the tubular packaging material by a forming roller 6, forms overlap by lapping both ends of the packaging material, longitudinally seals the overlap in the tube longitudinal direction by a longitudinal seal element 8 to form a longitudinal seal zone, fills liquid food into the tube from a filling pipe 7, sandwiches this tube by a sealing jaw 10 and an oppositely arranged jaw 11 while sending this tube downward by a length equivalent to one packaging container, forms two transversal seal zones by transversally sealing in the crossing direction, at the same time continuously forms pillow-like preliminary forming 12, cuts at the middle of the seal zone of the connected pillow-like preliminary forming by knife or the like to separate to individual pillow-like preliminary forming 13, bends flaps on the upper and lower of the separated pillow-like preliminary forming at a final folder 15 to form a finally shaped packaging filling container 14. The object to be inspected in this embodiment is a container obtained from this filling machine.

The examples of the obtained container are the rectangular solid liquid food filling paper-made container 14 and liquid food filling paper-made container whose center is octangular column similar to the former as shown in FIG. 3. The containers 14 have a folded transversal seal zone 23, container walls 22 and 22a and a longitudinal seal zone 26 running to the bottom face from the top wall 22a through the container wall on the back, and is provided with the flap 24 folded through the ridge side 24a.

In one embodiment according to this invention, a pre-processing unit rotates the flaps sealed to the container wall around a ridge side where the flaps integrally communicate with the container wall to peel the flaps from the container wall, returning to a shape of the pillow-like preliminary forming. More specifically, the above described container is returned to a shape of the pillow-like preliminary forming by rotating the flaps 24 and 25 sealed to the container wall around the ridge sides 24a and 25a where the flaps 24 and 25 integrally communicate with the container wall, and peeling from the container wall in a method substantially reverse to the method in which the flaps 24 and 25 are folded by the final folder 15 of the filling and packaging machine as shown in FIG. 2 by the pre-processing unit.

Figure 4:
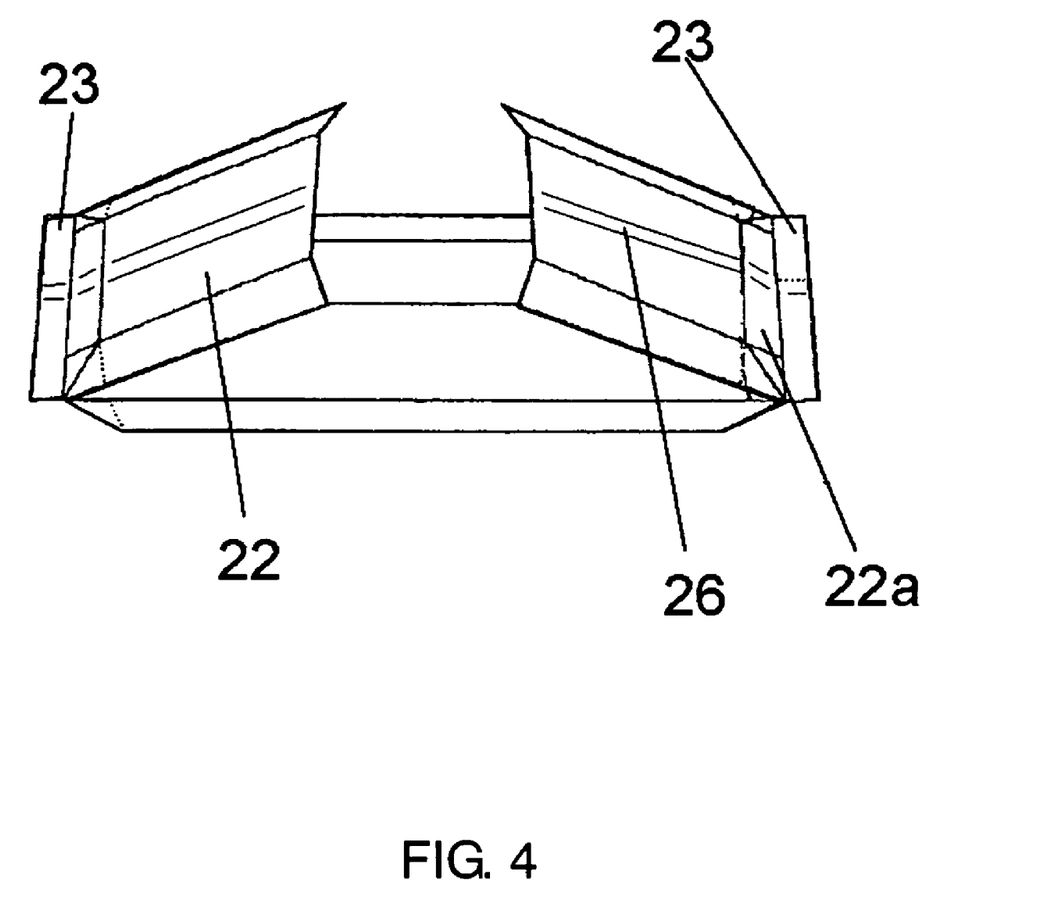
FIG. 4 is a perspective view of a sampled body according to one embodiment of this invention.
Figure 5:
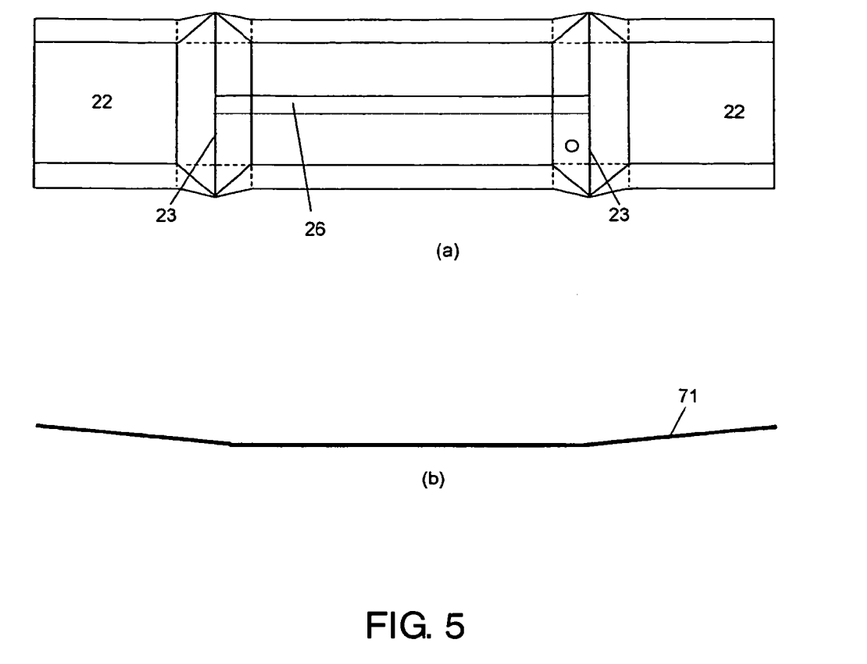
FIG. 5 is a plan and side view of a developed sampled body according to one embodiment of this invention.

Next, one face of the container wall 22 is cut in transversal direction by a cutting unit, and the filled food is taken out, and then the pillow-like preliminary forming is changed to plate-shape. Further the plate-shape forming is cut at both ends and then a sampled body as shown in FIG. 4 is made. The cut container wall is developed, the cut container is substantially developed to plane-like or the predetermined shape, and then the sampled body 71 as shown in FIG. 5(a), (b) is prepared by a preparing unit.

In one embodiment according to this invention, a seal quality unit measures electrostatic capacity and loss factor on the transversal seal zone and longitudinal seal zone of the sampled body for inspection. More specifically, alternating current is fed to portions to be inspected where seal status of the seal zone is intended to be inspected, and the seal status is inspected based on the electrostatic capacity and loss factor as an electric variable of the portions to be inspected at the time by the seal quality unit.

The seal quality unit in the embodiment according to this invention comprises a pair of first and second electrodes, a power supply device (AC) as an applying voltage generating part to generate alternating voltage applied to portions to be inspected, a current sensor as an electrical variable detecting part to detect electrostatic capacity and loss factor on the portion to be inspected, a detection processing part to perform processing for reading the voltage generated by said power supply device and the current detected by the current sensor, a control part consisting of CPU or the like to perform entire control of the seal status detecting device, a displaying device consisting of display or the like, an operation part for performing various operations, and a recording device or the like for recording the predetermined data. The current sensor detects alternate current flowing on the portion to inspected, and constitutes the current detecting part. In addition, a voltage sensor as a voltage detecting part is arranged, and the alternating current is detected as an electrical variable by the voltage sensor.

Figure 10:
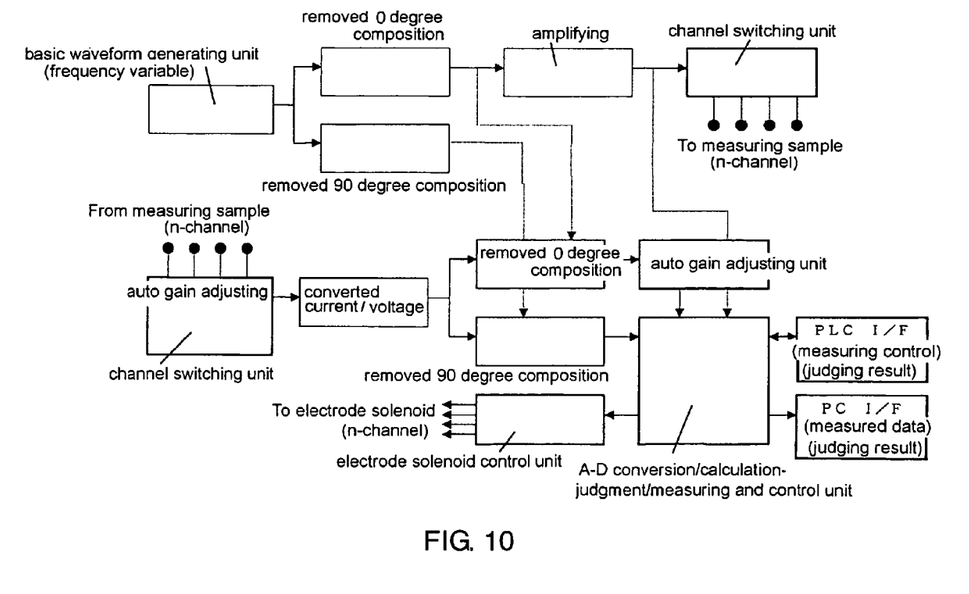
FIG. 10 is a block diagram of a seal quality judging device circuit according to one embodiment of this invention.

An example of circuit of a device to judge seal quality in the embodiment according to this invention will be shown. FIG. 10 is a block diagram of the circuit example. An outline of the circuit and control of the device to judge seal quality by measuring electrostatic capacity and loss factor on the heat seal part (seal zone) will be described with reference to FIG. 10. In this circuit example, a principle of LCR meter is utilized, and a function as an inspector is added to the function of LCR meter. After signal generated from a frequency variable basic waveform generating unit, whose zero degree composition is removed, is outputted and amplified, the signal is outputted to the predetermined measuring sample by a channel switching unit. It can be switched to n-channel in the channel switching unit. On the other hand, output from the measuring sample is received by an auto gain adjusting unit, is converted to current and voltage, then zero degree composition is removed. The removed signal is again auto gain adjusted, and sent to an A-D conversion/calculation-judgment/measuring and control unit together with a signal whose 90 degree composition is removed. Control signal is sent to the predetermined channel from the A-D conversion/calculation and judgment/measuring and control unit through an To electrode solenoid control unit. Measuring and control signal is sent to an interface of the PLC from the A-D conversion/calculation and judgment/measuring and control unit for measuring control after calculation and judgment. In addition, (measured data) and (judging result) are sent to an interface of computer (PC) from the A-D conversion/calculation and judgment/measuring and control unit.

The above aspect allows for measurement of electrostatic capacity and loss factor as a measuring function, and allows for selection of measuring frequency, measuring voltage, measuring average times and measuring channel for measurement. Additionally, for measurement, measuring gain is automatically switched so that error in measurement value is minimized. A judging function judges acceptable or unacceptable product based on the electrostatic capacity and loss factor, displays the result and records it together with the measured data to external recording equipment (such as PC). As control functions, there are provided measuring start control, and operation control function of measuring electrode by number of measuring channels, which are controlled by a single inspector or external control equipment (such PLC). The functions can be summarized to be relatively compact so that they can be integrated into the automatic inspection device according to the example of circuit of the device to judge the above described seal quality. A control software derives average value, maximum value and variance of the electrostatic capacity and loss factor as a calculating function to judge acceptable or unacceptable product. Further, as an option, measurement value when sample is absent can be also reflected on the judgment using a predetermined calculation standard value.

In one embodiment according to this invention, an overlap width on the seal inspected sampled body and unevenness on the external surface of the transversal seal zone edge on the inside of the container are measured by the image processing unit and inspected by image processing. For example, when positions of each edge side on both faces of the overlap on the sampled body are detected by the image processing unit and the overlap width is measured, a first edge side and/or a second edge side on the opposite side of the edge sides are made clear on the image processing. The edge portion on the inside of the container on transversal seal zone is measured for unevenness on the external surface over whole length of the external surface on the edge portion by the detecting unit, and acceptability of the transversal seal zone is judged by an analyzing unit based on signal from the detecting unit.

In one embodiment according to this invention, the first electrode is arranged at a distance from the seal zone of the sampled body, the second electrode is arranged so as to contact said sampled body, and damage (such as pinhole) on the seal zone is inspected by the seal damage inspection unit based on feedback current flowing on the second electrode. In this embodiment according to this invention, the first electrode (inspection electrode) applying inspection current to the sampled body is faced opposite to the longitudinal seal portion and/or the transversal seal portion on the sampled body, is arrange at the predetermined distance from the sampled body, and the second electrode (ground electrode) is arranged so as to contact the sampled body. The ground electrode always contacts the container (sampled body) during inspection. When inspection operation is started, for example, an inspection voltage of 8 to 12 [kV] is applied to the inspection electrode at a frequency of 500 [Hz]. Accompanying this, feedback current is transmitted to the analyzing unit through the second electrode (ground electrode). The analyzing unit detects said feedback current, inspects whether any damage occurs on the packaging container based on the detected feedback current, and then can judge acceptable or unacceptable product based on the inspection result.

In the embodiment according to this invention, whether any damage occurs on the sampled body is inspected based on the feedback current flowing on the second electrode. When an inspection voltage is applied to a sampled body on which no damage occurs by the inspection electrode, uniform corona discharge is generated to the sampled body 61. As most of electric energy of the inspection voltage is consumed accompanying this, only a small amount of charge remains on the sampled body. Accordingly, only a small amount of discharge current flows on the second electrode (ground electrode), then in this case, the analyzing unit judges that no damage occurs on the sampled body. On the contrary, when the inspection current is applied to a sampled body on which any damage occurs on the inspection electrode, intensive corona discharge is generated to the portion on the sampled body where any damage occurs. As electric energy of the inspection voltage is easily transmitted to the sampled body, a large amount of charge remains on the sampled body. Accordingly, a large amount of feedback current flows on the second electrode (ground electrode), and direct voltage is generated. If the generated DC voltage is higher than a threshold value, the analyzing unit judges that any damage occurs on the sampled body, and if the DC voltage is lower than the threshold value, the analyzing unit judges that no damage occurs on the sampled body. When it is judged that any damage occurs on the sampled body, the analyzing unit judges the sample body to be unacceptable product, and when it is judged that no damage occurs on the sampled body, it judges the sample body to be acceptable product.

The container inspection method of one embodiment according to this invention can process and store, further outputs the inspection results of seal quality inspection, inspection by image processing and inspection for damage on seal zone. In addition, the container inspection device of one embodiment according to this invention can comprise a control and sorting unit for controlling the seal quality unit, image processing unit and the seal damage inspection unit, receiving judging result according to the command signal and sorting said sample body according to acceptability of the judging result.

Figure 6:
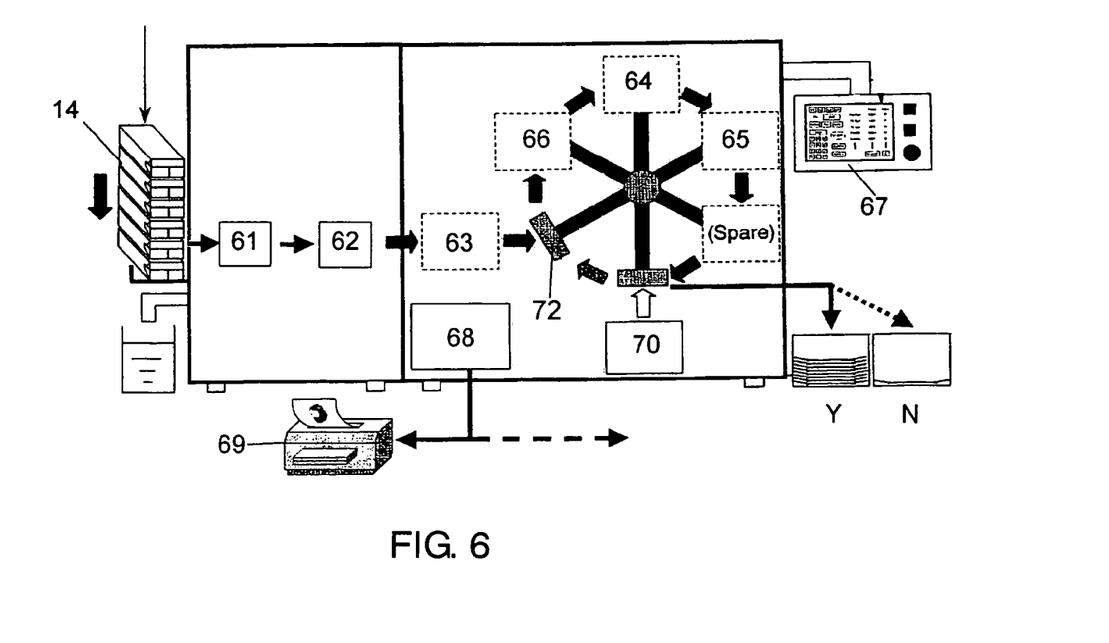
FIG. 6 is an entire schematic view of a container inspection device according to one embodiment of this invention.

A layout example of the container inspection device of one embodiment according to this invention will be described. FIG. 6 shows an entire block diagram of a container inspection system. The sample container 14 for inspection is fed to the pre-processing unit 61 and the sampled body preparing body 62 from the paper container producing machine (filling machine) as shown in FIG. 1. In this embodiment, after flap strength inspection (not shown) and simple seal continuity inspection (pressure test: not shown) are conducted, the container is processed to sampled body (paper piece of test piece). And then, various inspections are automatically performed on the test piece by the container inspection device of one embodiment according to this invention. The inspection device of this inspection comprises a seal inspection device for transversal seal (63), a seal inspection device for longitudinal seal (66), image processing unit (appearance inspection device, 64) and a seal damage inspection unit (pinhole inspection device, 65) or the like. The inspection result are informed and displayed through a touch panel 67, and at the same time accumulated into a data logger 68 (or higher computer). In addition, if necessary, the result can be also printed by a printer 69 and daily work report can be easily created. Furthermore, it is configured to be capable of printing ID No. on the test piece by an ink jet printer 70 or the like, and collating actual test piece with the data. The test pieces for which all processes are completed are automatically (classified into acceptable product Y and unacceptable product N and) put into storage box depending on the inspection result, and easily stored after that.

In the container inspection device of the above embodiment, the inspection device is configured in which each inspection is arranged in circle. A test piece 71 is closed until the sample container 14 is carried out from the pre-processing unit 61 and sampled body preparing unit 62 and fitted to a sampled body holder 72 (refer to FIG. 4). This is because it is easier to inspect in a state that the transversal seal (63) is closed. In addition, it is preferable to conduct the pinhole inspection (65) in the final process because it may damage the test piece. Advantages in arranging the inspections in circle are that electric and pneumatic wiring to the sampled body holder 72 are easily performed from the rotation center using slip ring or the like, and fixing/positioning operation of the test piece to the sampled body holder 72 is completed at one time. Even for embodiment to arrange in circle, there are two types of vertically arranging type (Ferris wheel type) shown in FIG. 6 and horizontally arranging type (merry-go-round type). The vertically arranging type is suitable when bottom area of the device is attempted to be reduced, and the horizontally arranging type is advantageous when height of the device is attempted to be shortened. Maintenance and inspection are easy for the horizontally arranging type because the inspection devices are arranged on a plane.

Figure 7:
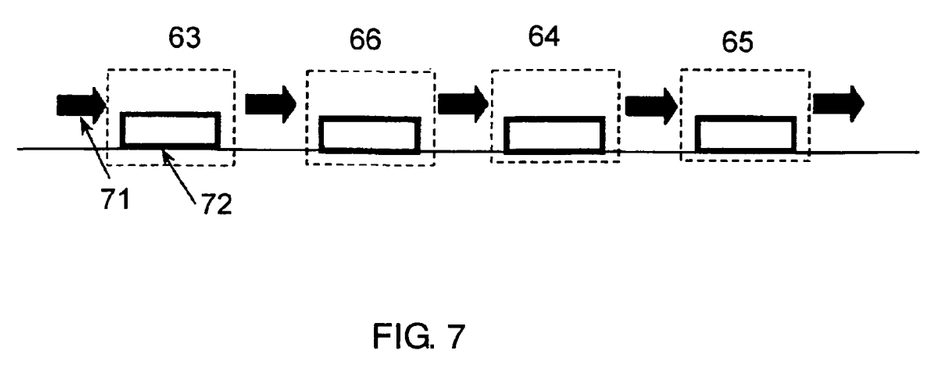
FIG. 7 is a schematic view of a container inspection device according to one embodiment of this invention.

FIG. 7 shows a second layout example of the inspection device according to this invention. In this embodiment, each inspection unit of the seal inspection device for transversal seal (63), seal inspection device for longitudinal seal (66), image processing unit (appearance inspection device, 64) and seal damage inspection unit (pinhole inspection device, 65) is arranged in series, and the test piece 71 is positioned at every time if necessary. For measurement of the seal inspection device (63), ground line can be used in low resistance, and accuracy can be enhanced. That is, it is advantageous that the ground line can be directly connected to an electrode for seal inspection device in the sampled body holder 72 not through slip ring and contact connector or the like. In this scheme, this is possible because the sampled body holder is fixed.

Figure 8:
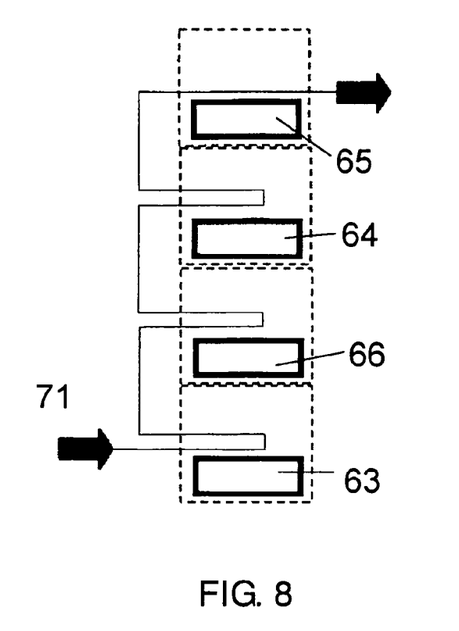
FIG. 8 is a schematic view of a container inspection device according to one embodiment of this invention.

FIG. 8 shows a third layout example of the inspection device according to this invention. This is derived from the scheme of the second layout example shown in FIG. 7. The seal inspection device for transversal seal (63), seal inspection device for longitudinal seal (66), image processing unit (appearance inspection device, 64) and seal damage inspection unit (pinhole inspection device, 65) are arranged in. parallel, and the test piece 71 is fitted to each inspection station and positioned at every time if necessary. There is an advantage that installing area can be minimized.

Figure 9:
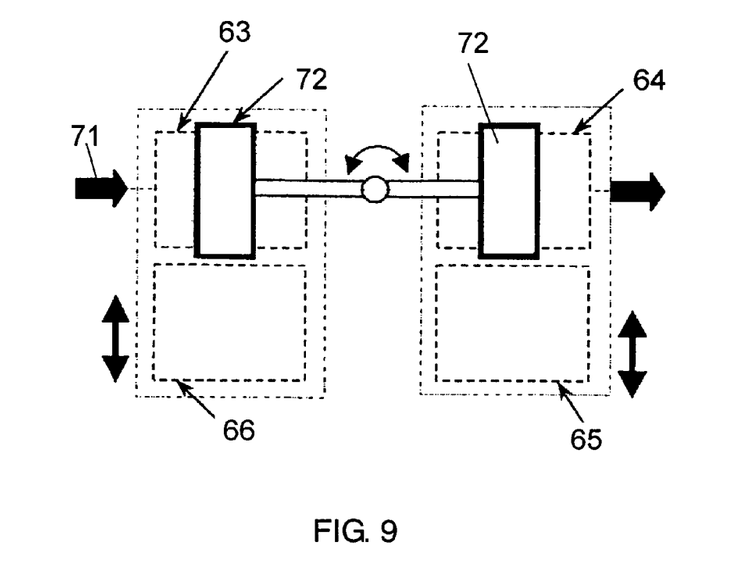
FIG. 9 is a schematic view of a container inspection device according to one embodiment of this invention.

FIG. 9 shows a fourth layout example of the inspection device according to this invention. In this example, there exist two sampled holders 72, which are structured to be capable of alternately rotating by +180 and −180 degrees. That is, electric system such as ground line for seal inspection device can be directly connected to the sampled body holders 72. The inspection unit is constituted to have respective two "inspection unit groups" (which can be increased if necessary) on both sides, and these two groups are structured to be capable of sliding in the direction of arrow in the FIG. 9. The measuring procedure is that the test piece 71 is fixed to the sampled body holder 72 with being closed, and is inspected by the seal inspection device for transversal seal (63). Further, if there exists any test piece in the sampled body holder 72 on the opposite side, it is inspected by the image processing unit (appearance inspection device, 64). When the test piece is developed as shown in FIG. 5 after inspection is ended, the inspection device slides and inspection can be made by the seal inspection device for longitudinal seal (66). In addition, if there exists any test piece on the opposite side, inspection can be also made by the seal damage inspection unit (pinhole inspection device, 65). When these inspections are ended, the sampled body holder 72 rotates, and on the opposite side, inspection is similarly performed by the image processing unit (appearance inspection device, 64) and seal damage inspection unit (pinhole inspection device, 65). Each inspection unit can be two-dimensionally arranged, therefore, there is an advantage that floor area can be effectively utilized and the entire system can be in compact size.

As described above, according to this invention, the following advantageous effects can be obtained.

According to the container inspection method and container inspection device of this invention, container quality can be inspected by a systematic and reasonable approach.

According to the container inspection method and container inspection device of this invention, human error such as missing when recording and error in writing can be eliminated without being influenced by operator's skillfulness.

According to the container inspection method and container inspection device of this invention, the result is objective and not based on operator's subjective judgment, and objective data can be statistically stored.

According to the container inspection method and container inspection device of this invention, labor load on operator can be alleviated. According to the container inspection method and container inspection device of this invention, variation due to experience and subjective view of operator can be eliminated, the obtained objective data can be systematically controlled by computer, and the data can be printed out to be used for daily work log, and can be used for data control of HACCP by further connecting to higher computer.

According to the preferred embodiment of the container inspection method and container inspection device of this invention, sampled body is given ID, then can be stored and easily controlled.

According to the preferred embodiment of the seal quality judging device circuit in the container inspection method and container inspection device of this invention, the devices can be organized in relatively compact size so as to be incorporated into automatic inspection equipment.

INDUSTRIAL APPLICABILITY

The container inspection method and container inspection device is used for inspecting quality of paper-made container or the like filled with liquid food such as juice and milk.

What is claimed is:

1. A container inspection method for inspecting quality of a finally shaped sealed container obtained by forming a web-like packaging laminated material having predetermined folding lines in tube shape, lapping both ends of the packaging material to form an overlap, longitudinally sealing the packaging material in the longitudinal direction to form an longitudinal seal zone on the overlap, filling food into the tube-shaped packaging material, pressing the packaging material at every predetermined interval in the crossing direction to seal the packaging material by the transversal seal to form a transversal seal zone, cutting at the middle of the transversal seal zone to obtain a pillow-like preliminary forming, and sealing flaps formed by folding along the folding lines to the container side wall and/or a container bottom face, comprising:

rotating the flaps sealed to the container wall around a ridge side where the flaps integrally communicate with the container wall to peel the flaps from the container wall;

returning to a shape of the pillow-like preliminary forming;

cutting the container wall and squeezing out the filled food to prepare a sampled body;

measuring electrostatic capacity and loss factor on said seal zone of the sampled body to inspect seal quality;

measuring an overlap width on the seal inspected sampled body and unevenness on the external surface of the transversal seal zone edge on the inside of the container by an image processing unit to inspect the overlap width and the unevenness by image processing;

arranging a first electrode at a distance from said seal zone of the sampled body;

arranging a second electrode so as to contact said sampled body; and inspecting damage on the seal zone based on feedback current flowing on the second electrode.

2. The container inspection method according to claim 1, comprising, processing inspection results of said seal quality inspection, inspection by image processing and inspection for damage on seal zone, storing as well as outputting.

3. A container inspection device for inspecting a finally shaped sealed container obtained by forming a web-like packaging laminated material having predetermined folding lines in tube shape, lapping both ends of the packaging material to form an overlap, longitudinally sealing the packaging material in the longitudinal direction to form an longitudinal seal zone on the overlap, filling food into the tube-shaped packaging material, pressing the packaging material at every predetermined interval in the crossing direction to seal the packaging material by the transversal seal to form a transversal seal zone, cutting at the middle of the transversal seal zone to obtain a pillow-like preliminary forming, and sealing flaps formed by folding along the folding lines to the container side wall and/or a container bottom face, comprising:

a pre-processing unit for rotating the flaps sealed to the container wall around a ridge side where the flaps integrally communicate with the container wall to peel the flaps from the container wall, and for returning to a shape of the pillow-like preliminary forming;

a sampled body preparing unit for cutting the container wall to protrude the filled food to prepare the sampled body;

a seal quality unit for measuring electrostatic capacity and loss factor on said seal zone of the sampled body to inspect seal quality;

a image processing unit for measuring an overlap width on the seal inspected sampled body and unevenness on the external surface of the transversal seal zone edge on the inside of the container to inspect the overlap width and the unevenness by image processing;

a seal damage inspection unit for arranging a first electrode at a distance from said seal zone of the sampled body, arranging a second electrode so as to contact said sampled body, and inspecting damage on the seal zone based on feedback current flowing on the second electrode.

4. The container inspection device according to claim 3, comprising a control sorting unit for controlling said seal quality unit, image processing unit and seal damage inspection unit, receiving judging result according to command signal and sorting said sampled body according to acceptability of the judging result.

* * * * *